United States Patent [19]

Webb et al.

[11] Patent Number: 5,274,158

[45] Date of Patent: Dec. 28, 1993

[54] PROCESS FOR STABILIZING SPENT SILICON CONTACT MASS

[75] Inventors: Steven W. Webb, Clifton Park; Alan Ritzer, Sand Lake; John D. Neely, Clifton Park, all of N.Y.

[73] Assignee: General Electric Company, Schenectady, N.Y.

[21] Appl. No.: 867,657

[22] Filed: Apr. 13, 1992

[51] Int. Cl.$^5$ .............................. C07F 7/08; C07F 7/16
[52] U.S. Cl. ........................................ 556/472; 502/56
[58] Field of Search ........................... 556/472; 502/56

[56] References Cited

U.S. PATENT DOCUMENTS

| | | | |
|---|---|---|---|
| 2,383,818 | 8/1945 | Rochow et al. | 556/672 |
| 4,724,122 | 2/1988 | Hosokawa | 419/35 |
| 4,892,694 | 1/1990 | Ritzer et al. | 264/109 |
| 5,000,934 | 3/1991 | Marko | 423/335 |

FOREIGN PATENT DOCUMENTS 3131732 2/1983 Fed. Rep. of Germany.

*Primary Examiner*—Paul F. Shaver
*Attorney, Agent, or Firm*—William A. Teoli; William H. Pittman

[57] ABSTRACT

A method is provided for passivating spent silicon contact mass by treating the spent silicon contact mass at a temperature in range of from 900° C. to 1500° C. in an inert atmosphere.

4 Claims, No Drawings

PROCESS FOR STABILIZING SPENT SILICON CONTACT MASS

Cross Reference to Related Application

This application relates to copending application 07/867,656, now U.S. Pat. No. 5,239,102, filed Apr. 13, 1992 and assigned to the same assignee as the present invention.

Background of the Invention

The present invention relates to a method for treating spent silicon contact mass generated during the production of organohalosilanes by the direct reaction of organic halide with silicon powder in the presence of a copper catalyst.

Prior to the present invention, the disposition of unused spent silicon contact mass, generated during the production of organohalosilane by the direct reaction between silicon powder and an organic halide, such as phenyl chloride or an alkyl halide for example methyl chloride, created a serious management problem for silicon manufacturers. Spent silicon contact mass, for example, upon removal from the reactor can be highly reactive in air and often ignites.

One method for passivating or stabilizing spent silicon contact mass which can have an average particle size in the range of about 1 micron to about 200 microns and at least 2% by weight of copper in the elemental or chemically combined state, is shown by Hosokawa, U.S. Pat. No. 4,724,122. Hosokawa combines the spent silicon powder with water, granulates the resulting mixture, and thereafter mixes the resulting granules with an inert inorganic powder. Another passivating technique for spent silicon contact mass is shown by Marko et al., U.S. Pat. No. 5,000,934, which employs a strong base at an elevated temperature to digest the hydrophobic siloxane rich coating on the spent silicon contact mass in order to dislodge the carbon coating which forms around the spent bed particles. An additional procedure for deactivating spent silicon contact mass is shown by Ritzer, et al., U.S. Pat. No. 4,892,694, which involves pelletizing the spent silicon contact mass and the impregnation of the pellets with an organic binder in aqueous carrier to stabilize the spent silicon contact mass to make it safe for transportation and disposal.

Additional processes are provided for the recovery of Rochow Synthesis mixtures derived from sludge vessels, as shown by Offenlegungschrift DE 313 1732AI and U.S. Pat. No. 4,758,352 to Felder et al. Mixtures of silicon solids and liquid containing polysilanes are subjected to a heat treatment or hydrolysis. For purposes of the invention, sludge vessel synthesis mixtures having a large proportion of liquid polysilanes are to be distinguished from the previously discussed pyrophoric spent silicon contact masses wherein liquid direct process high-boiling materials are not present as a constituent.

Although various procedures are available in the prior art for deactivating pyrophoric spent silicon contact mass generated during the direct method for making organohalosilanes, salvaging of the silicon and metallic values, such as copper, from the contact mass after the deactivation treatment is often not feasible. Additional procedures are therefore constantly being investigated to provide for safe handling of the spent silicon contact mass as well as the salvaging of the metallic values from the contact mass in a convenient manner.

Summary of the Invention

The present invention is based on the discovery that spent silicon contact mass can be rendered substantially non-reactive in air by heating the spent contact mass at a temperature in the range of about 900° C. to about 1400° C. under an inert atmosphere. Treatment time can vary depending upon such factors as the temperature used, the surface area of the spent contact mass and the weight percent of unreacted or elemental copper initially present in the spent contact mass. It has been found that annealed or stabilized spent silicon contact mass can then be safely handled and transported in bulk.

Statement of the Invention

There is provided by the present invention, a process for stabilizing spent silicon contact mass generated during the production of organohalosilanes by the reaction between powdered silicon and organic halide in the presence of a direct method catalyst comprising a copper catalyst, which process comprises treating the spent silicon contact mass at a temperature in the range of about 900° C. to about 1400° C. under an inert atmosphere until the spent silicon contact mass is rendered substantially nonreactive in air at temperatures up to 350° C.

Spent silicon contact mass in accordance with the present invention generally has a surface area of up to about 25 $M^2/g$. The spent silicon contact mass prior to treatment can be very reactive to both oxygen and methylchloride at temperatures exceeding 200° C.

Spent silicon contact mass which can be treated in the practice of the invention include materials shown by Marko et al., U.S. Pat. No. 5,000,934, Hosokawa, U.S. Pat. No. 4,724,122 and Ritzer et al., U.S. Pat. No. 4,892,694 which are incorporated herein by reference.

Prior to treatment, the spent silicon contact mass can be collected in a hopper under an inert atmosphere such as a nitrogen atmosphere. Alternatively, it can be conveyed directly to a thermal treatment or annealing zone shortly after it has been generated under direct process conditions. Suitable means for heating the spent silicon contact mass to an appropriate annealing temperature as previously defined, are for example, a calcining furnace or a rotary kiln. Venting of reaction gases such as surface chlorosilanes during treating also can be effected by the employment of an inert gas, such as nitrogen, or a noble gas, for example, argon. Effective treatment can be effected at temperatures in the range of from 900° C. to 1500° C. A temperature of about 1000° C. to 1200° C. is preferred and a temperature of about 1050° C. to 1100° C. is particularly preferred. Treating times in the range of from about 0.05 to 1 hours or more can be used depending upon the temperature employed and the spent powder properties. Spent silicon contact mass has been treated in accordance with the practice of the invention when it is nonreactive in air at temperatures up to 350° C. Nonreactive means that the treated spent contact mass can be safely transported or stored. Nonreactive also means that treated spent contact mass can exhibit an oxidative weight increase which does not exceed about 1.0% based on the total weight of treated mass after it has been exposed in air at a temperature maintained at about 400° C. for a period of up to about 15 minutes.

In order that those skilled in the art will be better able to practice of the present invention, the following examples are given by way of illustration and not by way of limitation. All parts are by weight.

A 200 milligram sample of spent silicon contact mass having about 10% by weight of elemental copper based on elemental analysis was placed in a gravimetric microbalance within a furnace. Air was passed over the sample as it was heated to a temperature of 400° C. The mass of the powder was monitored with time and temperature. After 15 minutes, the weight up take of the powder due to oxidation was found to increase to a constant value of about 7.8%.

A 50 g sample of spent silicon contact mass was placed in a quartz tube. Nitrogen was flowed through the powder at 5-50 cubic centimeters per second while the powder was uniformly heated to 1000°-1200° C. for about 3 minutes. The powder was then cooled to room temperature under flowing nitrogen to provide "treated" spent silicon contact mass.

A 200 milligram sample of the above treated spent silicon contact mass was then tested for oxidation uptake as described above. It was found that after 15 minutes of exposure at 400° C. in air the weight uptake of the treated spent silicon contact mass was 0.6-0.9% as compared to 7.8 weight % uptake prior to treatment.

Example 2

The procedure of Example 1 was repeated except that several spent silicon contact mass samples were heated at temperatures in the range of 450° C. to 1100° C. under flowing nitrogen. The degree of passivation of the heated spent silicon contact mass samples at temperatures between 25° C. to 1100° C. was determined by measuring their respective oxidation uptake potentials in terms of weight % oxygen uptake in air at temperatures to 400° C. for 15 minutes following the heat treatment. The following were the results obtained:

| Treatment of Contact Mass | | Oxidation Potential |
| --- | --- | --- |
| °C. | Time (hrs) | % Uptake to 400° C. |
| 25 | 0 | 3.3-7.8 |
| 1100 | 0.1 | 0.3 |
| 1000 | 0.1 | 0.25 |
| 900 | 0.1 | 0.41 |
| 600 | 3 | 2.2 |
| 450 | 48 | 2.6 |

The above results show that satisfactory passivation of the contact mass is effected at temperatures in the range of 900°-1100° C.

Example 3

A 20 g batch of spent silicon contact mass was placed in a 3.5 centimeter diameter glass container. A thermocouple was placed in the center of the powder and the powder was heated slowly to 400° C. The temperature of the powder was monitored during the heating period. As the temperature of the spent silicon contact mass was raised above 50° C., the bed produced white smoke. Visible combustion began at a temperature of about 110° C. as evidenced by significant evolution of white and yellow smoke and glowing of the powder surface. A solid aggregated mass was eventually obtained when the powder was allowed to cool to room temperature.

A 200 mg sample of spent silicon contact mass was uniformly heated in a glass tube to 400° C. in nitrogen. The tube was rapidly removed to expose the hot powder to air. The powder was found to be pyrophoric. It smoked and glowed within 1 minute of air exposure. A flame also briefly appeared above the surface of the powder.

The above procedure was repeated with spent silicon contact mass which was treated in accordance with the invention. It was evaluated for its oxidation weight % uptake potential in air as well as its pyrophoric properties. It was found that the oxidation weight % uptake potential of the treated powder was approximately 0.3-0.5%, which was less than 10% of the oxidation weight % uptake potential of the untreated silicon contact mass. In addition, there was no visible smoking or glowing within the mass of powder at temperatures up to 350° C. in air.

Although the above examples are directed to only a few of the very many variables which can be employed in the practice of the method of the present invention, it should be understood that the present invention is directed to a much broader variety of treatment conditions and spent silicon contact masses as shown in the description preceding these examples.

What is claimed is:

1. A process for treating spent silicon contact mass having a particle size in the range of about 1 to about 200 microns generated during the production of organohalosilanes by the reaction between powdered silicon and organic halide in the presence of a direct method catalyst comprising a copper catalyst, which process comprises heating the spent silicon contact mass at a temperature in the range of about 900° C. to about 1500° C. in an inert atmosphere for 0.05 to 1 hour until the spent silicon contact mass is renderd substantially nonreactive in air at temperatures up to 350° C.

2. A process in accordance with claim 1, where the spent silicon contact mass is generated during the production of methylchlorosilane.

3. A process for treating spent silicon contact mass in accordance with claim 1, wherein the temperature is 1000° C. to 1200° C.

4. A process for treating spent silicon contact mass in accordance with claim 1, wherein nitrogen is used to maintain an inert atmosphere.

* * * * *